United States Patent [19]
Martin

[11] Patent Number: 5,961,485
[45] Date of Patent: *Oct. 5, 1999

[54] COAXIAL DUAL LUMEN CATHETER

[75] Inventor: Geoffrey S. Martin, Mississauga, Canada

[73] Assignee: Vas-Cath Incorporated, Mississauga, Canada

[*] Notice: This patent is subject to a terminal disclaimer.

[21] Appl. No.: 08/943,070

[22] Filed: Oct. 2, 1997

Related U.S. Application Data

[63] Continuation of application No. 08/581,685, Dec. 29, 1995, abandoned, which is a continuation of application No. 08/264,285, Jun. 23, 1994, Pat. No. 5,480,380, which is a continuation of application No. 08/031,982, Mar. 16, 1993, abandoned.

[51] Int. Cl.$^6$ .................................................. A61M 3/00
[52] U.S. Cl. ........................ 604/43; 604/280; 604/283; 604/284
[58] Field of Search ................ 604/43, 93, 264, 604/280, 284, 283

[56] References Cited

U.S. PATENT DOCUMENTS

| | | | |
|---|---|---|---|
| 4,493,696 | 1/1985 | Uldall | 604/43 |
| 4,776,841 | 10/1988 | Catalano | 604/43 |
| 4,968,307 | 11/1990 | Dake et al. | 604/43 |
| 5,207,648 | 5/1993 | Gross | 604/264 |
| 5,360,397 | 11/1994 | Pinchuk | 604/43 |
| 5,380,276 | 1/1995 | Miller et al. | 604/43 |

*Primary Examiner*—Wynn Wood Coggins
*Assistant Examiner*—Jennifer R. Sadula
*Attorney, Agent, or Firm*—Trask, Britt & Rossa

[57] ABSTRACT

The invention provides a dual lumen catheter comprising outer and inner tube materials. A main portion extends axially and has a selected first cross-section. The main portion includes main portions of the respective outer and inner tube materials which together define an annular intake lumen and a main part of a return lumen contained inside the intake lumen. A tubular transition portion is made up integrally of both the outer and inner tube materials and has a second cross-section smaller than the first cross-section. The transition portion extends axially from the distal end of the main portion and this can be extended to include a tip portion made up only of outer tube material and which extends axially from the transition portion. The transition portion on its own, or with the tip portion, defines a tip section which is a continuation of said main part of the return lumen to complete the return lumen.

56 Claims, 3 Drawing Sheets

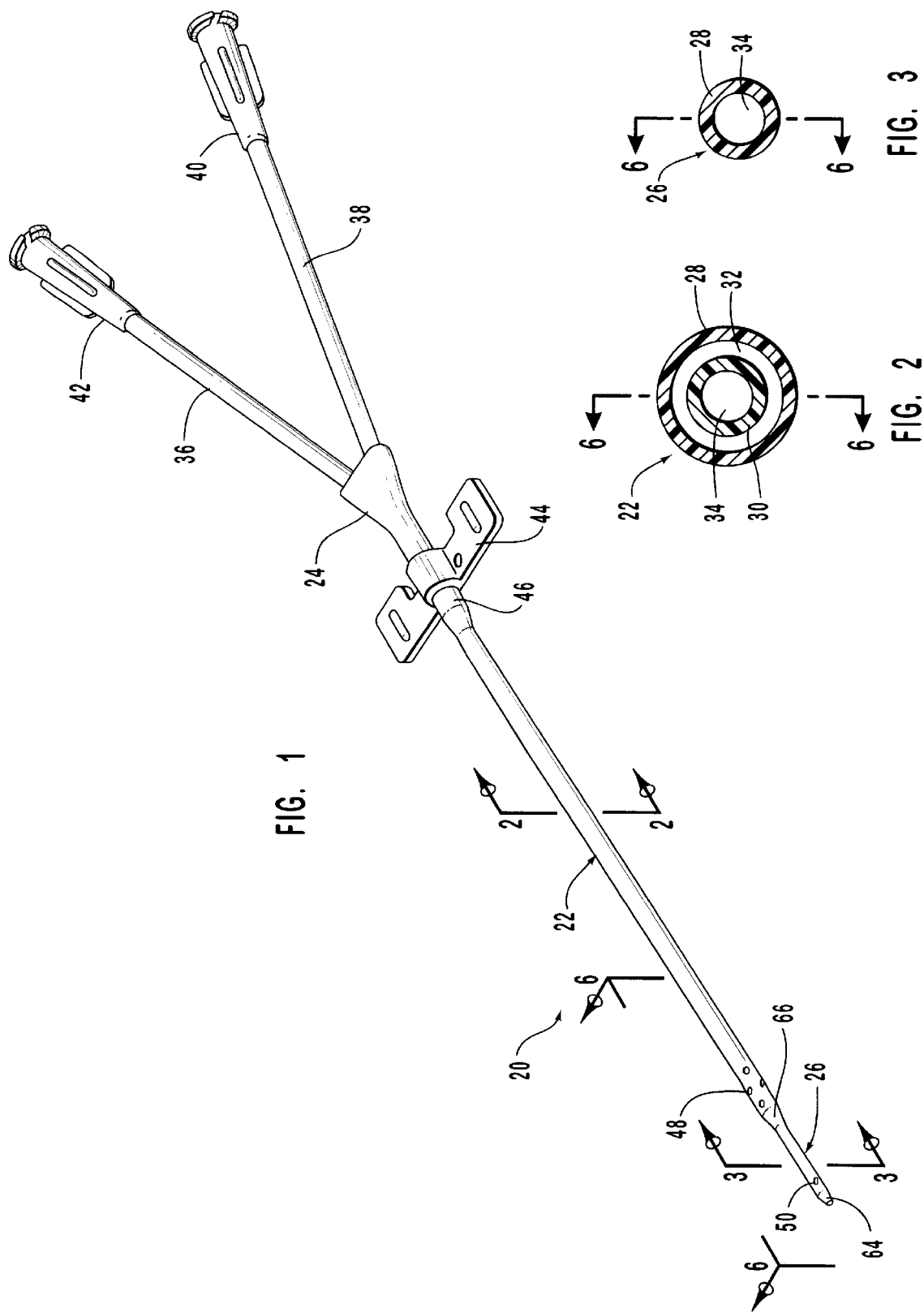

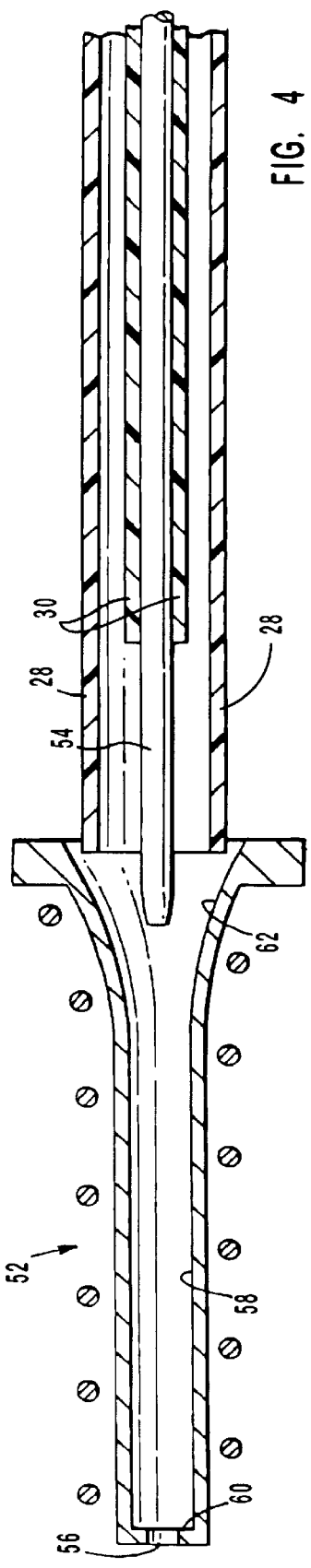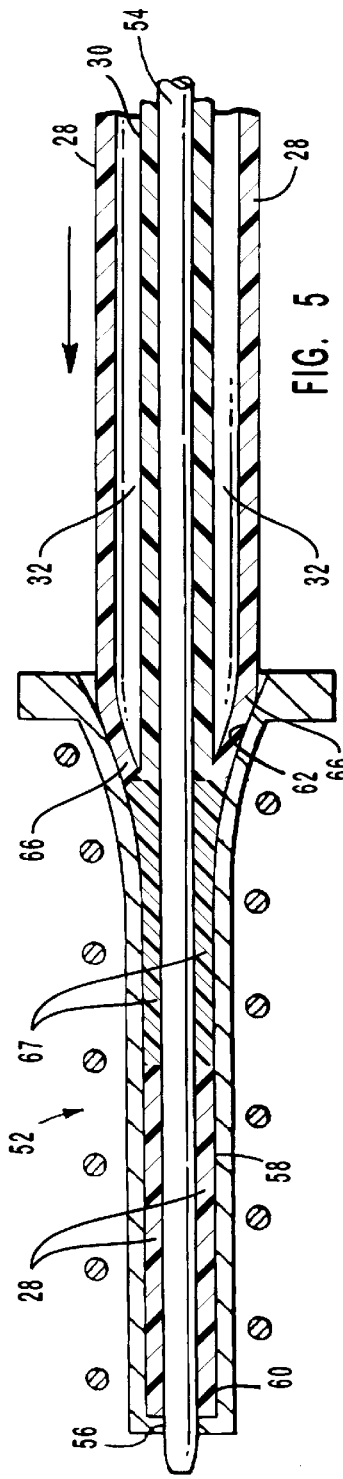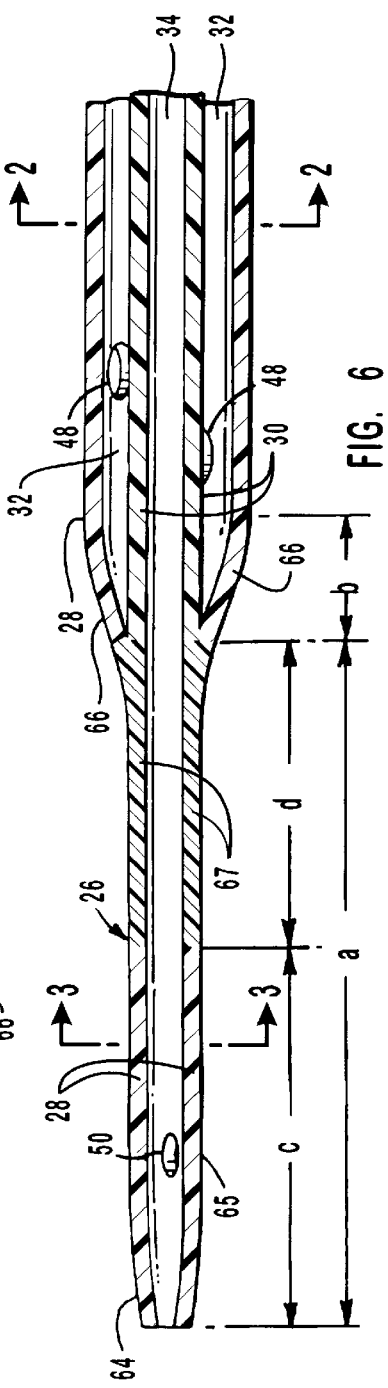

COAXIAL DUAL LUMEN CATHETER

This application is a continuation of U.S. patent application Ser. No. 581,685 filed on Dec. 29, 1995, now abandoned which was a continuation of U.S. patent application Ser. No. 264,285 that was filed on Jun. 23, 1994, and that issued as U.S. Pat. No. 5,480,380, which was in turn a continuation of U.S. patent application Ser. No. 31,982 filed on Mar. 16, 1993, and now abandoned.

BACKGROUND

1. The Field of the Invention

This invention relates to dual lumen catheters for use in haemodialysis treatments and more particularly to a dual lumen catheter having coaxial intake and return lumens.

2. Background Art

Haemodialysis treatments have been developed since the early 1960s using a variety of combinations and arrangements of catheters. The earliest treatments were conducted using two needles in the same vein and this subsequently led to pioneer work done by Dr. Shaldon in England who used two flexible catheters which could be left in place for limited periods. Some practioners proposed the use of a dual flow catheter because this could be entered through a single incision rather than two. From this two basic types were developed. One was a coaxial catheter with the intake lumen surrounding the return lumen, and the other a catheter having side-by-side lumens either in individual tubes connected to one another or in a single extrusion defining two lumens.

Catheters having side-by-side lumens have the disadvantages that because the lumens are side-by-side, the intake openings can be in one side of the catheter only. As a consequence of this, if the catheter were to attach itself to the wall of a vein due to suction applied to the intake lumen, then of course the flow would stop. Medical staff then have to move the catheter by rotating it until blood again flows. This is a very delicate manipulation which is normally performed only by a qualified medical practioner who must be available at all times in case the flow is discontinued.

This disadvantage has resulted in renewed interest in coaxial devices which can be made to have openings in any part of the wall of the catheter. As a result, no matter where the catheter may rest against a vein, some of the intake openings remain patent. There is then less likelihood that during use the catheter must be serviced by a trained medical practioner.

Coaxial catheters are subject to design criteria which can be dificult to meet and which may have contributed to the initial popularity of side-by-side structures. Because the coaxial catheter is inherently less resistant to kinking than side-by-side structures, the tubes used in the structure have had relatively thick walls with the result that the catheter had to also have a larger cross-sectional area than an equivalent side-by-side catheter. One of the reasons for this is that typically the inner tube projected beyond the outer tube to form a distal tip section. Because of this the cross-section of the inner tube has to be chosen to have sufficient rigidity to permit engagement over a Seldinger wire. This consideration set the size of the inner tube.

Another approach is taught by U.S. Pat. No. 4,493,696 to Uldall. The catheter shown in this patent was designed specifically to permit removal of the inner tube between treatments. It was thought at the time of the patent (that is in about 1980) that such a procedure would be desirable. However, it is now accepted that with modern techniques it is not necessary to remove the inner tube. Also, the inherent disadvantages of accidental separating of the tubes, accurate location of one tube relative to the other, sizing, and the sudden change of section at the end of the inner tube, were all obstacles to the use of this catheter.

SUMMARY OF THE INVENTION

The present catheter uses a structure which permits a relatively thin walled inner tube to be used to minimize the overall cross-section of the catheter. Also, the inner tube meets the tip section smoothly to provide a continuous inner lumen at a transition portion where the inner and outer tube materials meet in a permanent bond to minimize the risk of accidental separation and to ensure repeatable manufacturing methods for more constant catheter structures.

Accordingly, in one of its aspects, the invention provides a dual lumen catheter comprising outer and inner tube materials. A main portion extends axially and has a selected first cross-section. The main portion includes main portions of the respective outer and inner tube materials which together define an annular intake lumen and a main part of a return lumen contained inside the intake lumen. A tubular transition portion, is made up integrally of both the outer and inner tube materials and has a second cross-section smaller than the first cross-section. The transition portion extends axially from the distal end of the main portion and this can be extended to include a tip portion made up only of outer tube material and which extends axially from the transition portion. The transition portion on its own, or with the tip portion, defines a tip section which is a continuation of said main part of the return lumen to complete the return lumen.

BRIEF DESCRIPTION OF THE DRAWINGS

This invention will be better understood with reference to the drawings in which:

FIG. 1 is an isometric view of a preferred embodiment of a catheter according to the invention;

FIG. 2 is a sectional view on line 2—2 in FIG. 1 and drawn to a larger scale;

FIG. 3—3 is a sectional view on line 3—3 of FIG. 1 and drawn to the same scale as FIG. 2;

FIG. 4 is a diagrammatic view of a step in the manufacture of a distal end of the catheter;

FIG. 5 is a view similar to FIG. 4 and showing a subsequent step in the manufacture of the distal end;

FIG. 6 is a sectional view on line 6—6 in FIG. 1 of a finished distal end of the catheter shown therein;

DESCRIPTION OF THE PREFERRED EMBODIMENT

Figures 7, 8:
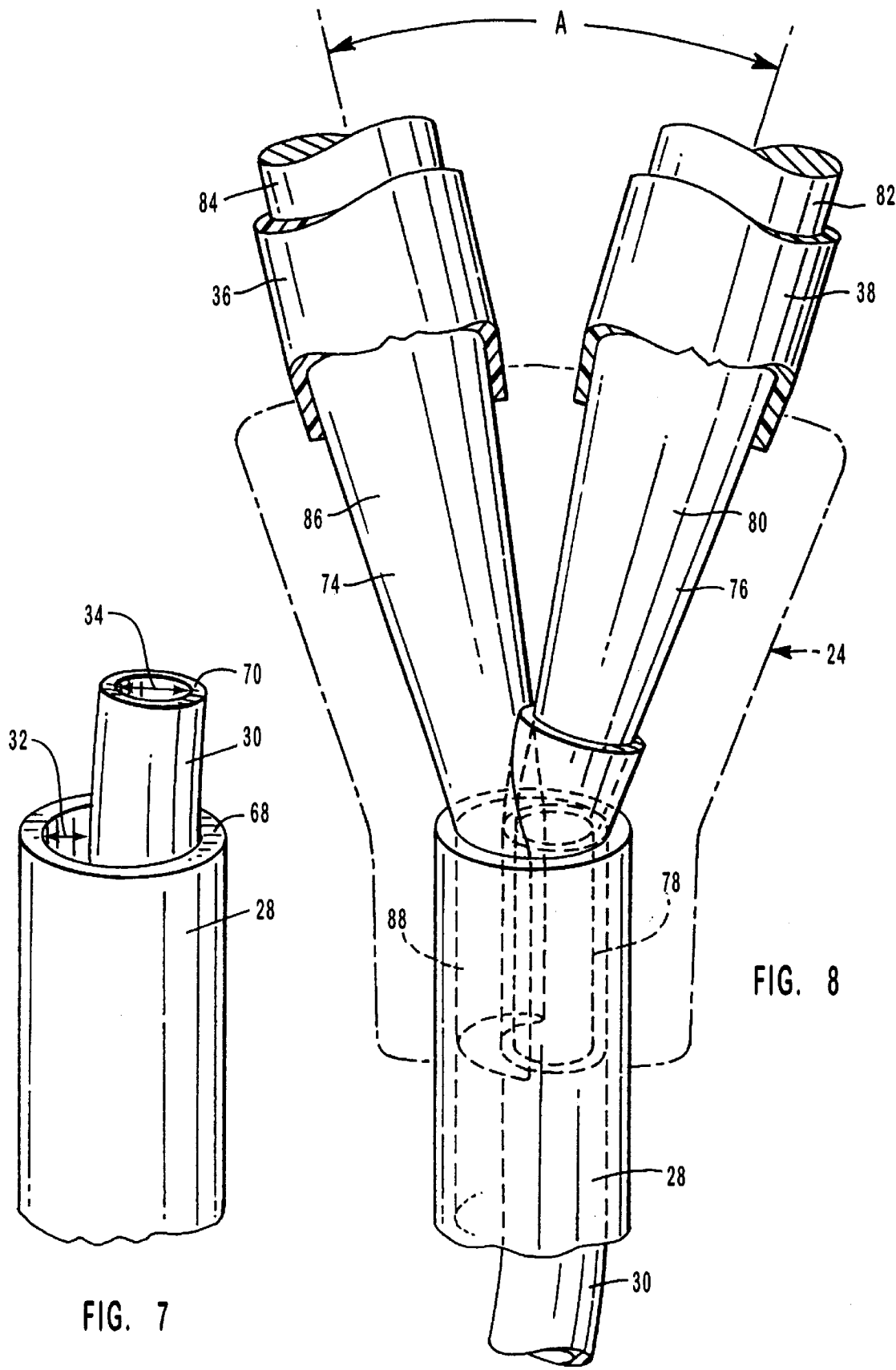
FIG. 7 is an isometric view of a proximal end of the main portion of the catheter during manufacture of the proximal end.
FIG. 8 is a diagrammatic representation of the proximal end prepared ready for moulding a connector at the proximal end of the main body.

Reference is first mace to FIG. 1 which illustrates a catheter designated generally by the numeral 20 and consisting of the main portion 22 extending from a trident shaped connector 24 to a distal tip section 26. As seen in FIG. 2, the main portion 22 is made up of an outer tube material 28 and an inner tube material 30 spaced radially from one another to define an annular intake lumen 32 and a circular return lumen 34. The return lumen 34 continues beyond the main portion 22 and into the tip section 26 as indicated by the section at FIG. 3. However, there is a transition between the main portion 22 and the tip section involving both the outer and inner tube materials 28, 30 as will be described.

At the proximal end, the trident shaped connector 24 has connected to it respective intake and return tubes 36, 38 having the usual luer fittings 40, 42 to make connection to tubing associated with a dialysis machine or the like.

The connector 24 has internal channels connecting the tubes 36, 38 to the respective lumens 32, 34 (FIG. 2) as will be described more fully with reference to FIGS. 7 and 8.

The catheter is completed by the inclusion of a rotatable suture wing 44 mounted on the main section and held in place by a collar 46 locating the suture wing 44 against the connector 24 for longitudinal positioning of the suture wing 44.

As also seen in FIG. 1, the catheter has side openings 48, 50. The openings 48 are spaced circumferentially around the catheter to provide access to the intake lumen 32 and optional side openings 50 are provided adjacent the distal end of the catheter to permit a flow from the return lumen 34.

The structure of the tip section 26 will be better understood with reference to the method of manufacture which is illustrated in FIGS. 4 and 5.

Reference is next made to FIG. 4 which is a diagrammatic illustration of the early steps in the manufacture of the tip section. As seen in FIG. 4, outer tube material 28 in the form of an extruded round tube is positioned adjacent a RF heating device 52 and contains inner tube material 30 also in the form of an extruded tube of round cross-section. This latter tube has a thinner wall than the outer tube, but this is not shown in order to simplify the drawings.

The material 30 contains a round stainless steel mandrel 54 which projects beyond the distal extremity of the outer tube material 28 and is shaped for engagement in an opening 56 at the inner end of RF heating device 52. RF heating device 52 has an internal shape matching that of the required tip section 26 of catheter 20 and includes a tubular main portion 58 extending outwardly from a back wall 60 containing the opening 56, and ending at flared entrance 62 which blends into the main portion 58 with a curvature to be given to the catheter. It will be seen that the inner tube material 30 has an inner diameter matching the outer diameter of the mandrel 54 and the distal end of the inner tube material 30 terminates inwardly of the distal end of the outer tube material 28 by a distance equal to about one quarter of the length of the cavity in the RF device 52.

Preferably each of outer and inner tube materials 28, 30 is a thermoplastic material.

Once the parts are arranged as shown in FIG. 4, the RF device 52 is energized to heat the device to a temperature sufficient to cause flow in the outer and inner tube materials 28, 30. Once heating has been achieved, the parts shown in FIG. 4 are moved into RF heating device 52 in unison, and this movement continues until they take up the position shown in FIG. 5. It will be evident from the arrangement in FIG. 4 that the end of the mandrel 54 is first engaged in the opening 56 and then the distal end of the outer tube material 28 meets the wall 60 and this ensures that the material about the mandrel forms a constant wall thickness. While this is happening, the distal end of the inner tube material 30 will meet the converging outer wall material 28 and because of the heat, the two will blend into one over a significant length of RF heating device 52, indicated by a separate and closer form of cross-hatching in FIG. 5. This is better illustrated in FIG. 6.

As seen in FIG. 6, tip section 26 has a length "a" which may include a tapered tip 64 formed either during or after the procedure described with reference to FIGS. 4 and 5. The purpose of this is simply to improve the utility of the catheter in association with a Seldinger wire which is fed through the centre of the catheter.

As also seen in FIG. 6, the tip section 26 is made up of tip portion 64 having a length "c" and a transition portion 67 having a length "d" corresponding to the closer cross-hatching mentioned with reference to FIG. 5. Tip portion 64 is made up of the outer tube material 28 whereas portion 67 is made up of both outer and inner tube materials 28, 30. There is also a tapered portion 66 having a length "b" made up of the outer tube material 28.

This arrangement of manufacture permits a relatively light thin walled inner tube material 30 to be used within more robust outer tube material 28. The resulting return lumen 34 (FIG. 2) is smooth walled and continuous and is made up of outer tube material 28 at the tip portion 64, both outer and inner tube materials 28, 30 at the transition portion 67, and of the inner tube material 28 alone over the main portion of the return lumen corresponding to portion 22 (FIG. 1) of the catheter.

As mentioned, it is desirable that the inner tube material 30 have a relatively thin wall in order to minimize the space lost to flow within the outer tube 28, and consequently to reduce the area of cross-section of the catheter. Because the outer tube material 28 is sufficiently robust, it can be used adventageously to form the tip portion 64.

It will also be appreciated that because the outer tube material 28 is being reduced in diameter as it is deformed, it will lengthen. Consequently the length of the tip section is a function of the reduction in diameter and wall thickness.

Reference is next made to FIGS. 7 and 8 which illustrate a method of making the connector 24 and also show details of the connector. As seen in FIG. 7, proximal ends 68, 70 of the outer and inner tube materials 28, 30 are positioned so that the inner tube material projects outwardly beyond the outer tube material. With this arrangement, a pair of first and second mandrels 74, 76 are engaged as shown in FIG. 8. The first mandrel 76 has a leading cylindrical portion 78 blending outwardly into a converging and generally conical portion 80, which in turn blends into, and cylindrical portion 82 angled with respect to the leading cylindrical portion 78. The cylindrical portion 78 is engaged in the inner tube material 30 and pushed into place so that there is a slight flaring of this material as it engages on the conical portion 80.

Mandrel 74 is then engaged. This mandrel has an outer cylindrical portion 84 which blends into a converging and generally conical portion 86 ending at a projection 88. This projection has a generaly U-shaped configuration and is angled with respect to the conical portion 86.

The projection 88 on the end of the mandrel 74 is shaped to fit the space provided when the inner tube material 30 is held against the inner surface of the outer tube material 28. (i.e. in the position shown in FIG. 7). As a result there is a generally U-shaped space between the inner and outer tube materials which is filled by the projection 88. The angular offsets of the cylindrical portion 78 of mandrel 76 and the projection 88 of mandrel 74 result in these parts extending axially with respect to the catheter while outer cylindrical portions 82, 84 of the mandrels diverge at an angle "A" indicated in FIG. 8. These cylindrical parts receive respective intake and return tubes 36 and 38 which are positioned as shown in FIG. 8. Once the assembly shown in FIG. 8 has been completed, the mould is closed and injection takes place to form the connector 24 shown in chain-dotted outline. This outline of course also represents the cavity of the mould.

The material used for all of the parts is preferably polyurethane, including the moulded connector 24, although other materials can be used provided that the usual requirements of compatibility, etc. are met.

After moulding and cooling, the mandrels 74, 76 are removed and because there is flexibility in the material, and because the mandrels are smooth, the mandrels can be pulled out without causing any damage.

It will be evident that this arrangement of connector provides for a smooth transition from the respective intake and return tubes 36, 38 to the respective intake and return lumens 32, 34 (shown in FIG. 2) in the main body of the catheter.

It is significant to note that the angle "A" shown in FIG. 8 can be kept to a small angle in the order of 15 to 20 degrees and is readily maintained below 30 degrees. As a result, the flow into and out of the catheter is essentially axial with reference to the main section 28 at all times. This is desirable in situations where the catheter has to be positioned such that the connecting tubes 36, 38 are as near in line with the catheter as possible.

In a typical catheter to be used for haemodialysis, this inner tube material 28 has an outside diameter of 11.5 French and a wall thickness of 0.45 mm, and the inner tube material has an outside diameter of 6.5 French and a wall thickness of 0.19 mm. The dimensions shown in FIG. 6 are approximately: a=30 mm; b=4 mm; c=17 mm; and d=13 mm. The distance between the ends of the outer and inner tube materials 28, 30 in FIG. 4 is about 6 mm and the travel in the RF device 52 is about 25 mm resulting in about 2–3 mm increase in length.

One possible variation from the preferred embodiment is to arrange for the distal end of the catheter to coincide with the distal end of the transition portion 67 shown in FIG. 6, however it is preferred to include the tip portion 65.

It is clear that the preferred embodiment described is exemplary of the coaxial lumen catheters generally and that the details and dimensions given are for example only. Such other structures are within the scope of the invention as claimed.

I claim:

1. A dual lumen catheter comprising:
   (a) a catheter body having a proximal end and a distal end, said catheter body comprising:
      (i) an inner tube comprised of an inner tube material and enclosing a first lumen open at said proximal end and at said distal end of said catheter body;
      (ii) an outer tube comprised of an outer tube material enclosing said inner tube, thereby defining a second lumen between said inner tube and said outer tube, said second lumen being open at said proximal end of said catheter body;
      (iii) a distal extremity of said catheter body, the interior of said outer tube converging radially inwardly at said distal extremity of said catheter body into contact with said inner tube, thereby terminating the distal extent of said second lumen; and
   (b) a tubular transition portion extending distally from said distal extremity of said catheter body at which said inner tube is permanently secured to said outer tube, said transition portion being comprised of said inner tube material and said outer tube material blended into an integral structure, and said transition portion having an open distal end, an open proximal end, and an outer cross section smaller than the outer cross section of said outer tube, said open proximal end of said transition portion communicating smoothly and continuously with said first lumen at said distal extremity of said catheter body.

2. A catheter as recited in claim 1, further comprising means for effecting fluid communication individually with said proximal end of each of said first lumen and said second lumen.

3. A catheter as recited in claim 1, wherein said catheter body is free of bends.

4. A catheter as recited in claim 1, further comprising a tubular tip portion extending distally from said distal end of said transition portion, said tip portion comprising:
   (a) an outer cross section substantially similar to said outer cross section of said transition portion;
   (b) an open distal end;
   (c) an open proximal end, said open proximal end of said tip portion communicating smoothly and continuously with said open distal end of said transition portion.

5. A catheter as recited in claim 4, wherein said tip portion is comprised of said outer tube material and is substantially free of said inner tube material.

6. A catheter as recited in claim 5, wherein said tip portion is comprised exclusively of said outer tube material.

7. A catheter as recited in claim 4, wherein said tip portion is integrally formed with said transition portion.

8. A catheter as recited in claim 4, wherein the outer cross section of said tip portion is circular.

9. A catheter as recited in claim 4, wherein said open distal end of said tip portion is circular.

10. A catheter as recited in claim 4, wherein said tip portion further comprises an integrally formed tubular distal extremity at said open distal end of said tip portion.

11. A catheter as recited in claim 10, wherein said distal extremity of said tip portion is comprised of said outer tube material and is substantially free of said inner tube material.

12. A catheter as recited in claim 11, wherein said distal extremity of said tip portion is comprised exclusively of said outer tube material.

13. A catheter as recited in claim 10, wherein said distal extremity of said tip portion is conical.

14. A catheter as recited in claim 10, wherein said distal extremity of said tip portion comprises:
   (a) an open distal end corresponding to said open distal end of said tip portion; and
   (b) an open proximal end, said open proximal end of said distal extremity of said tip portion communicating smoothly and continuously through said tip portion with said open distal end of said transition portion.

15. A catheter as recited in claim 14, wherein the outer cross section of said distal extremity of said tip portion tapers radially inwardly in a direction toward said open distal end thereof.

16. A catheter as recited in claim 4, further comprising an opening formed through the outer wall of said tip portion, said opening formed through said outer wall of said tip portion thereby communicating between the exterior and the interior of said tip portion.

17. A catheter as recited in claim 16, wherein said opening formed through said outer wall of said tip portion is circular.

18. A catheter as recited in claim 16, wherein said opening formed through said outer wall of said tip portion is located proximal of said distal end of said tip portion.

19. A catheter as recited in claim 1, wherein the outer cross section of said distal extremity of said catheter body tapers inwardly from said outer tube of said catheter body to said transition portion.

20. A catheter as recited in claim 19, wherein said distal extremity of said catheter body is conical.

21. A catheter as recited in claim 1, further comprising an opening formed through the outer wall of said outer tube said catheter body, said opening formed through said outer wall of said outer tube thereby communicating between the exterior of said outer tube and said second lumen.

22. A catheter as recited in claim 21, wherein said opening formed through said outer wall of said outer tube is circular.

23. A catheter as recited in claim 21, wherein said opening formed through said outer wall of said outer tube is located proximal of said distal extremity of said catheter body.

24. A catheter as recited in claim 1, wherein the outer cross section of said inner tube is circular.

25. A catheter as recited in claim 1, wherein the outer cross section of said outer tube is circular.

26. A catheter as recited in claim 1, wherein said first lumen is circular.

27. A catheter as recited in claim 1, wherein said second lumen is annular.

28. A catheter as recited in claim 1, wherein the outer cross section of said transition portion is circular.

29. A catheter as recited in claim 1, wherein said catheter body is substantially straight.

30. A cardiovascular access catheter comprising:
    (a) a catheter body having a proximal end and a distal end, said catheter body comprising:
        (i) an inner tube of circular outer cross section comprised of an inner tube material and enclosing a first lumen open at said proximal end and at said distal end of said catheter body;
        (ii) an outer tube of circular outer cross section comprised of an outer tube material enclosing said inner tube, thereby defining a second lumen between said inner tube and said outer tube, said second lumen being open at said proximal end of said catheter body;
        (iii) a conical distal extremity of said catheter body, the interior of said outer tube converging radially inwardly at said distal extremity of said catheter body into contact with said inner tube, thereby terminating the distal extent of said second lumen; and
    (b) a tubular transition portion extending distally from said distal extremity of said catheter body at which said inner tube is permanently secured to said outer tube, said transition portion being comprised of said inner tube material and said outer tube material blended into an integral structure, and said transition portion having an open distal end, an open proximal end, and an outer cross section smaller than the outer cross section of said outer tube, said open proximal end of said transition portion communicating smoothly and continuously with said first lumen at said distal extremity of said catheter body;
    (c) a tubular tip portion extending distally from said distal end of said transition portion, said tip portion being comprised of said outer tube material and being substantially free of said inner tube material, and said tip portion comprising:
        (i) an outer cross section substantially similar to said outer cross section of said transition portion;
        (ii) an open distal end;
        (iii) an open proximal end, said open proximal end of said tip portion communicating smoothly and continuously with said open distal end of said transition portions; and
        (iv) a conical tubular distal extremity of said tip portion extending distally therefrom and being integrally formed therewith;
    (d) a bifurcation hub attached to said outer tube and to said inner tube at said proximal end of said catheter body;
    (e) a first catheter access tube attached to said bifurcation hub and communicating therethrough to said first lumen at said proximal end of said catheter body; and
    (f) a second catheter access tube attached to said bifurcation hub and communicating therethrough to said second lumen at said proximal end of said catheter body.

31. A catheter as recited in claim 30, wherein said distal extremity of said catheter body tapers inwardly from said outer tube of said catheter body to said transition portion.

32. A catheter as recited in claim 30, wherein said distal extremity of said tip portion comprises:
    (a) an open distal end corresponding to said open distal end of said tip portion; and
    (b) an open proximal end, said open proximal end of said distal extremity of said tip portion communicating smoothly and continuously through said tip portion with said open distal end of said transition portion, the outer cross section of said distal extremity of said tip portion tapering radially inwardly in a direction toward said open distal end thereof.

33. A catheter as recited in claim 30, wherein said first catheter access tube at said bifurcation hub and said second catheter access tube at said bifurcation hub are symmetrically disposed relative to the longitudinal axis of said catheter body at said proximal end thereof.

34. A catheter as recited in claim 30, wherein said tip portion is comprised exclusively of said outer tube material.

35. A catheter as recited in claim 30, where the thickness of the wall of said inner tube is less than the thickness of the wall of said outer tube.

36. A cardiovascular access catheter comprising:
    (a) a catheter body having a proximal end and a distal end, said catheter body comprising;
        (i) an inner tube comprised of an inner tube material and enclosing a first lumen open at said proximal end and at said distal end of said catheter body;
        (ii) an outer tube comprised of an outer tube material enclosing said inner tube, thereby defining a second lumen between said inner tube and said outer tube, said second lumen being open at said proximal end of said catheter body;
        (iii) a conical distal extremity of said catheter body, the interior of said outer tube converging radially inwardly at said distal extremity of said catheter body into contact with said inner tube, thereby terminating the distal extent of said second lumen; and
    (b) a tubular transition portion extending distally from said distal extremity of said catheter body at which said inner tube is permanently secured to said outer tube, said transition portion being comprised of said inner tube material and said outer tube material blended into an integral structure, and said transition portion having an open distal end, an open proximal end, and an outer cross section smaller than the outer cross section of said outer tube, and said open proximal end of said transition portion communicating smoothly and continuously with said first lumen at said distal extremity of said catheter body; and (c) a tubular tip portion extending distally from said distal end of said transition portion, said tip portion comprising:
  (i) an outer cross section substantially similar to said outer cross section of said transition portion;
  (ii) an open distal end;
  (iii) an open proximal end, said open proximal end of said tip portion communicating smoothly and continuously with said open distal end of said transition portions; and
  (iv) a tubular distal extremity of said tip portion extending distally therefrom and being integrally formed therewith.

37. A catheter as recited in claim 36, further comprising means for effecting fluid communication individually with said proximal end of each of said first lumen and said second lumen.

38. A catheter as recited in claim 37, wherein said means for effecting fluid communication comprises:
  (a) a bifurcation hub attached to said outer tube and to said inner tube at said proximal end of said catheter body;
  (b) a first catheter access tube attached to said bifurcation hub and communicating therethrough to said first lumen at said proximal end of said catheter body; and
  (c) a second catheter access tube attached to said bifurcation hub and communicating therethrough to said second lumen at said proximal end of said catheter body.

39. A catheter as recited in claim 38, wherein said bifurcation hub, said first catheter access tube, and said second catheter access tube are comprised of a common thermoplastic material.

40. A catheter as recited in claim 38, wherein an outer surface of said inner tube engages an inner surface of said outer tube at said bifurcation hub.

41. A catheter as recited in claim 38, wherein said bifurcation hub is trident-shaped.

42. A catheter as recited in claim 38, wherein said first catheter access tube at said bifurcation hub forms a divergence angle with said second catheter access tube at said bifurcation hub.

43. A catheter as recited in claim 42, wherein said divergence angle is less than about 30°.

44. A catheter as recited in claim 43, wherein said divergence angle is a range from about 15° to about 20°.

45. A catheter as recited in claim 38, wherein said means for effecting fluid communication also establishes essentially axial fluid flow into and out of said proximal end of said catheter body through each of said first catheter access tube and said second catheter access tube, respectively.

46. A catheter as recited in claim 45, wherein each of said first catheter access tube and said second catheter access tube at said bifurcation hub is essentially aligned with said proximal end of catheter body.

47. A catheter as recited in claim 46, wherein said first catheter access tube at said bifurcation hub forms a divergence angle with said second catheter access tube at said bifurcation hub.

48. A catheter as recited in claim 47, wherein said divergence angle is less than about 30°.

49. A catheter as recited in claim 48, wherein said divergence angle is a range from about 15° to about 20°.

50. A catheter as recited in claim 45, wherein said first catheter access tube at said bifurcation hub and said second catheter access tube at said bifurcation hub are symmetrically disposed relative to the longitudinal extent of said catheter body at said proximal end thereof.

51. A catheter as recited in claim 50, said first catheter access tube at said bifurcation hub forms a divergence angle with said second catheter access tube at said bifurcation hub.

52. A catheter as recited in claim 51, wherein said divergence angle is less than about 30°.

53. A catheter as recited in claim 52, wherein said divergence angle is a range from about 15° to about 20°.

54. A catheter as recited in claim 38, wherein said bifurcation hub is comprised of a thermoplastic material bonded to said first catheter access tube and said second catheter access tube.

55. A catheter as recited in claim 36, wherein said tip portion is comprised of said outer tube material and is substantially free of said inner tube material.

56. A catheter as recited in claim 55, wherein said tip portion is comprised exclusively of said outer tube material.

* * * * *

UNITED STATES PATENT AND TRADEMARK OFFICE
CERTIFICATE OF CORRECTION

PATENT NO.  : 5,961,485
DATED       : October 5, 1999
INVENTOR(S) : Geoffrey S. Martin It is certified that error appears in the above-identified patent and that said Letters Patent is hereby corrected as shown below:

<u>Column 2,</u>
Line 61, change "mace" to -- made --.

<u>Column 4,</u>
Line 65, change "These cylindrical parts" to -- Cylindrical portions 82,84 --.

Signed and Sealed this

Twenty-sixth Day of March, 2002

Attest:

JAMES E. ROGAN
Attesting Officer    Director of the United States Patent and Trademark Office